(12) United States Patent
Campbell et al.

(10) Patent No.: US 10,485,583 B2
(45) Date of Patent: Nov. 26, 2019

(54) ENDOSCOPIC ULTRASOUND FINE NEEDLE FIDUCIAL SYSTEM

(71) Applicant: COVIDIEN LP, Mansfield, MA (US)

(72) Inventors: Eugene Campbell, Natick, MA (US); John O. McWeeney, Brighton, MA (US); Brian Tinkham, Scituate, MA (US); Stephen J. Tully, Waltham, MA (US)

(73) Assignee: Covidien LP, Boulder, CO (US)

( * ) Notice: Subject to any disclaimer, the term of this patent is extended or adjusted under 35 U.S.C. 154(b) by 258 days.

(21) Appl. No.: 15/284,683

(22) Filed: Oct. 4, 2016

(65) Prior Publication Data

US 2017/0100162 A1    Apr. 13, 2017

Related U.S. Application Data

(60) Provisional application No. 62/238,242, filed on Oct. 7, 2015.

(51) Int. Cl.
*A61B 17/34* (2006.01)
*A61B 90/00* (2016.01)

(52) U.S. Cl.
CPC ...... *A61B 17/3468* (2013.01); *A61B 17/3417* (2013.01); *A61B 17/3478* (2013.01); *A61B 90/03* (2016.02); *A61B 90/39* (2016.02); *A61B 2017/3419* (2013.01); *A61B 2017/3443* (2013.01); *A61B 2090/034* (2016.02); *A61B 2090/0807* (2016.02); *A61B 2090/0811* (2016.02); *A61B 2090/3925* (2016.02);
(Continued)

(58) Field of Classification Search
CPC ......... A61N 1/05; A61M 36/12; A61M 37/00; G08B 1/08; A61B 19/00

USPC .............................. 600/7; 607/122; 606/117
See application file for complete search history.

(56) References Cited

U.S. PATENT DOCUMENTS

| 4,498,482 A | 2/1985 | Williams |
| 5,279,570 A | 1/1994 | Dombrowski et al. |
| | (Continued) | |

FOREIGN PATENT DOCUMENTS

| CA | 1150580 | 7/1983 |
| EP | 1935373 A2 | 6/2008 |
| | (Continued) | |

OTHER PUBLICATIONS

Examination report No. 1 for AU App. No. 2016238906, dated Feb. 20, 2017, from the Australian Government IP Australia.
(Continued)

*Primary Examiner* — Jon Eric C Morales
(74) *Attorney, Agent, or Firm* — Holland & Hart LLP

(57) ABSTRACT

Methods, apparatuses and systems are described for implanting a plurality of fiducial markers into a tissue. Systems include a needle, a stylet sized to slide within a lumen of the needle, and a multi-stop stylet spacer having stopping features configured to engage with the stylet to stop the distal end of the stylet at one or more predetermined distances from the distal end of the needle. Methods for implanting a plurality of fiducial markers into a tissue are described and include inserting a needle preloaded with fiducial markers into a tissue, adjusting a multi-stop stylet spacer from a safety position to a first deployment position, deploying a first fiducial marker into the tissue, adjusting the stylet spacer from the first deployment position to a second deployment position, and deploying a second fiducial marker into the tissue.

14 Claims, 12 Drawing Sheets

(52) U.S. Cl.
CPC ................ *A61B 2090/3966* (2016.02); *A61B 2090/3987* (2016.02)

(56) References Cited

U.S. PATENT DOCUMENTS

| | | | |
|---|---|---|---|
| 5,810,769 | A | 9/1998 | Schlegel et al. |
| 2003/0199760 | A1 | 10/2003 | Curpen et al. |
| 2009/0209804 | A1 | 8/2009 | Seiler |
| 2009/0270797 | A1 | 10/2009 | Aubert et al. |
| 2009/0299384 | A1 | 12/2009 | Iida et al. |
| 2010/0331677 | A1 | 12/2010 | Hong et al. |
| 2012/0116248 | A1 | 5/2012 | McWeeney |
| 2014/0121677 | A1 | 5/2014 | Clancy et al. |
| 2014/0243844 | A1 | 8/2014 | Clancy et al. |
| 2014/0371586 | A1 | 12/2014 | Ryan et al. |

FOREIGN PATENT DOCUMENTS

| | | |
|---|---|---|
| EP | 2520237 A1 | 11/2012 |
| EP | 2609872 A2 | 7/2013 |
| EP | 2981309 A1 | 2/2016 |
| JP | H07100140 A | 4/1995 |
| JP | 2008521527 A | 6/2008 |
| JP | 2010012212 A | 1/2010 |
| JP | 2012525215 A | 10/2012 |
| JP | 2015506761 A | 3/2015 |
| WO | 0128631 A1 | 4/2001 |
| WO | 2010126750 A2 | 11/2010 |
| WO | 2013116142 A1 | 8/2013 |

OTHER PUBLICATIONS

Extended European Search report for EP Application No. 16192691.0 from the European Patent Office dated Jul. 4, 2017.

English translation of Japanese Office action dated Sep. 20, 2017, for Patent Application No. 2016-197946, from the Japanese Patent Office.

Partial Search Report for Application No. 16192691.0 dated Mar. 15, 2017 from the European Patent Office.

Examiner's Report for Canadian Application No. 2,944,259, dated Feb. 2, 2018, from the Canadian Intellectual Property Office.

English translation of Chinese Office Action dated Jan. 17, 2018, for Patent Application No. 201510593299.0, from the Chinese Patent Office.

Examination Report for Australian Application No. 2018200018 dated Nov. 21, 2018 from IP Australian.

Jun. 1, 2018 Notice of Allowance for Japanese Application No. 2016-197946.

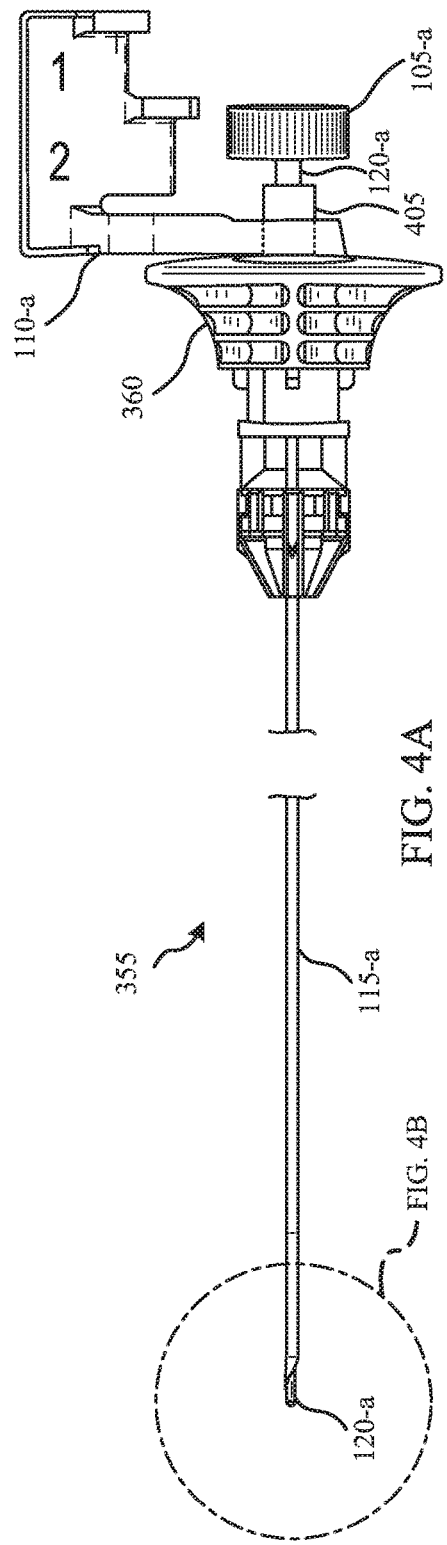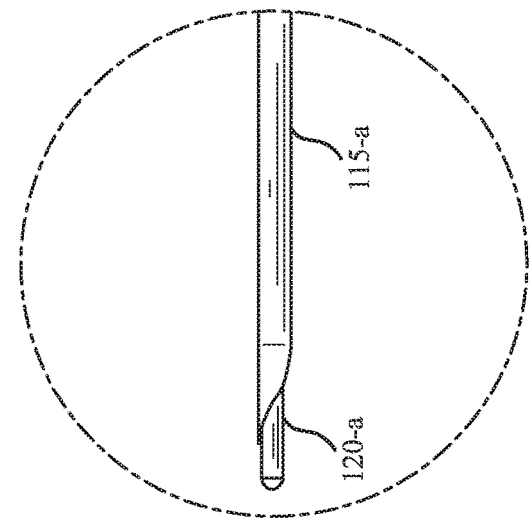
FIG. 4A
FIG. 4B

ENDOSCOPIC ULTRASOUND FINE NEEDLE FIDUCIAL SYSTEM

CROSS REFERENCES

The present Application for Patent claims priority to U.S. Provisional Patent Application No. 62/238,242 by Campbell et al., entitled "ENDOSCOPIC ULTRASOUND FINE NEEDLE FIDUCIAL SYSTEM," filed Oct. 7, 2015, assigned to the assignee hereof, and which is hereby expressly incorporated by reference herein in its entirety.

BACKGROUND

Radiation therapy is sometimes used to treat cancerous tissue within the human body. During radiation therapy, a radiation source external to the body is aimed at the target tissue to be treated within the body. Due to patient movement during the procedure, the radiation source sometimes misses the target tissue and adversely affects surrounding, healthy tissue. To increase the accuracy of the radiation source and to reduce damage to surrounding tissue, Image-Guided Radiotherapy (IGRT) is sometimes used. In such procedures, the target tissue is marked, either with a skin tattoo or an implantable fiducial marker, and the radiation source is directed towards that marker.

Typically, to implant a fiducial marker into a target tissue, a clinician will load the fiducial marker into either the sharp end (distal end) or the back end (proximal end) of a hollow needle, insert the needle into a delivery system such as an endoscope and maneuver the needle to the target tissue, puncture the target tissue with the needle, and inject the fiducial marker into the target tissue with a stylet. It is often desirable to implant two or more fiducial markers at different locations within the target tissue so that the precise location of the target tissue can be determined through triangulation techniques. Accordingly, after implanting the first fiducial marker, the clinician typically must completely remove the needle from the delivery system, manually reload the sharp end of the contaminated needle with a second fiducial marker, reinsert the needle through the delivery system to reach a different location within the target tissue, and then implant the second fiducial marker with the stylet. In some instances, the entire delivery system is removed from the body each time a new fiducial marker is loaded into the needle. This process is repeated until all of the fiducial markers are implanted.

Repeatedly removing the needle from the delivery system and manually reloading each of the fiducial markers into the needle one at a time may be difficult and cumbersome due to the small size of the fiducial markers and may also increase the duration of the procedure and the risk of injury to both the patient and the clinician. Alternatively, if the clinician instead loads several fiducial markers into the back end of the needle at once, it may be difficult to push the fiducial markers all the way through the needle with the stylet. If the clinician instead loads the fiducial markers into the sharp end of the needle, there is an increased risk of accidental needle stick and disease transmission to the clinician. In any case, when multiple fiducial markers are loaded into the needle, it may be difficult for the clinician to controllably implant a single fiducial marker at a time to achieve adequate spacing between each implanted fiducial marker instead of accidently implanting multiple fiducial markers in one location within the target tissue.

SUMMARY

The described features generally relate to one or more improved methods, systems, and devices for implanting multiple fiducial markers into tissue. In accordance with various aspects of the present disclosure, a device for implanting a plurality of fiducial markers into a tissue is described. The device may include a needle having a proximal end, a distal end, and a lumen extending therebetween and a stylet having a proximal end and a distal end. The distal end of the stylet is sized to slide within the lumen of the needle. The device may also include a multi-stop stylet spacer having a plurality of stopping features configured to engage with the stylet to stop the distal end of the stylet at a plurality of predetermined distances from the distal end of the needle.

In certain aspects, the multi-stop stylet spacer is adjustable between a plurality of positions by actuating the multi-stop stylet spacer in a plane orthogonal to the proximal end of the stylet. In such examples, the proximal end of the stylet may engage with a different stopping feature in each of the plurality of positions.

According to some examples, the multi-stop stylet spacer is adjustable between three positions. In a first position the proximal end of the stylet may engage a first stopping feature to stop the distal end of the stylet in a first location with respect to the distal end of the needle. In a second position the proximal end of the stylet may engage a second stopping feature to stop the distal end of the stylet in a second location located distal to the first location, and in a third position the proximal end of the stylet may engage a third stopping feature to stop the distal end of the stylet in a third location located distal to the second location.

In some examples, the device includes a plurality of fiducial markers housed within the lumen of the needle, wherein in the first position the first stopping feature prevents deployment of any of the plurality of fiducial markers from the distal end of the needle and in the second position the second stopping feature permits the deployment of a first of the plurality fiducial markers while preventing the deployment of a second of the plurality of fiducial markers.

The plurality of predetermined distances from the distal end of the needle may be based on a number and a size of a plurality of fiducial markers housed within the lumen of the needle. In certain examples, the plurality of stopping features of the multi-stop stylet spacer comprises a plurality of ledges arranged in a stair-stepped configuration.

Additionally or alternatively, the device further includes a plurality of fiducial markers housed within the lumen of the needle separated by at least one fiducial marker spacer. The fiducial markers may be textured or dogbone shaped. Moreover, the device may also include a fiducial marker retention member coupled with the distal end of the needle. According to certain examples, the fiducial marker retention member comprises bone wax, or a cap configured to fit over the distal end of the needle, or one or more detents disposed within the lumen of the needle, or any combination of these features. In some examples, the stylet is tapered such that the distal end has a smaller diameter than the proximal end.

In accordance with certain aspects of the disclosure, a system for implanting a plurality of fiducial markers into a tissue is described. The system may include a handle member assembly having a proximal end, a distal end, and a lumen extending therebetween and a sheath having a proximal end, a distal end, and a lumen extending therebetween where the proximal end of the sheath is coupled with the distal end of the handle member assembly to form a continuous lumen from the proximal end of the handle member to the distal end of the sheath. The system may also include a needle having a proximal end, a distal end, and a lumen extending therebetween and being sized to advance through the continuous lumen of the handle member assembly and the sheath. A plurality of fiducial markers may be housed within the lumen of the needle. In addition, the system may include a stylet having a proximal end and a distal end and sized to advance through the lumen of the needle and a multi-stop stylet spacer having a plurality of stopping features configured to engage with the stylet to controllably deploy the plurality of fiducial markers from the distal end of the needle.

According to certain examples of the system, a first of the plurality of stopping features engages with the stylet to prevent the stylet from deploying any of the plurality of fiducial markers from the distal end of the needle. In such examples, a second of the plurality of stopping features may engage with the stylet to permit the stylet to deploy a first fiducial marker from the distal end of the needle, and wherein a third of the plurality of stopping features engages with the stylet to permit the stylet to deploy a second fiducial marker from the distal end of the needle.

In accordance with certain aspects, the multi-stop stylet spacer of the system is adjustable between a plurality of positions by actuating the multi-stop stylet spacer in a plane orthogonal to the proximal end of the stylet. In such examples, the proximal end of the stylet may engage with a different stopping feature in each of the plurality of positions.

In a particular example, the multi-stop stylet spacer is adjustable between three positions such that in a first position the proximal end of the stylet engages a first stopping feature to stop the distal end of the stylet to prevent any of the plurality of fiducial markers from being deployed from the distal end of the needle; in a second position the proximal end of the stylet engages a second stopping feature to stop the distal end of the stylet to permit the deployment of a first of the plurality fiducial markers while preventing the deployment of a second of the plurality of fiducial markers; and in a third position the proximal end of the stylet engages a third stopping feature to stop the distal end of the stylet to permit the deployment of the second of the plurality of fiducial markers. According to some examples, the plurality of stopping features of the multi-stop stylet spacer comprise a plurality of ledges arranged in a stair-stepped configuration.

In some examples, the system further includes at least one fiducial marker spacer disposed between at least two of the plurality of fiducial markers. In addition, the system may include a fiducial marker retention member coupled with the distal end of the needle. According to certain aspects, the distal end of the handle member may be configured to couple with an endoscope.

In accordance with various examples, a method for implanting a plurality of fiducial markers into a tissue is described. The method may include providing a fiducial marker implantation device comprising a needle, a plurality of fiducial markers housed within the needle, a stylet, and a multi-stop stylet spacer. The method may further include inserting the needle into the tissue, adjusting the stylet spacer from a safety position to a first deployment position, and deploying a first fiducial marker into the tissue by advancing the stylet distally until the stylet spacer engages with and stops the stylet. In various examples, the method further includes adjusting the stylet spacer from the first deployment position to a second deployment position and deploying a second fiducial marker into the tissue by advancing the stylet distally. In accordance with various examples, the multi-stop stylet spacer comprises a plurality of stopping features that engage with and stop the stylet in each of the safety and first deployment positions.

Certain examples of the present disclosure may include some, all, or none of the above advantages or features. One or more other technical advantages or features may be readily apparent to those skilled in the art from the figures, descriptions, and claims included herein. Moreover, while specific advantages or features have been enumerated above, various examples may include all, some, or none of the enumerated advantages or features.

Further scope of the applicability of the described methods and apparatuses will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

A further understanding of the nature and advantages of the examples may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 4A is an illustration of a subassembly of a fiducial marker delivery device in accordance with aspects of the present disclosure;

FIG. 4B is a detailed view of a subassembly of a fiducial marker delivery device in accordance with aspects of the present disclosure;

DETAILED DESCRIPTION

The present disclosure is generally directed to devices, systems, and methods for implanting multiple fiducial markers into diseased tissue in preparation for image-guided radiotherapy (IGRT). In accordance with various examples, a device may include a needle, a stylet, and a stylet spacer configured to facilitate the controlled deployment of multiple fiducial markers into a tissue.

Examples of the present disclosure are now described in detail with reference to the drawings. As used herein, the term "clinician" refers to a doctor, nurse, or any other care provider and may include support personnel. The term "proximal" will refer to the portion of the device or component thereof that is closer to the clinician and the term 'distal" will refer to the portion of the device or component thereof that is farther from the clinician.

Figure 1:
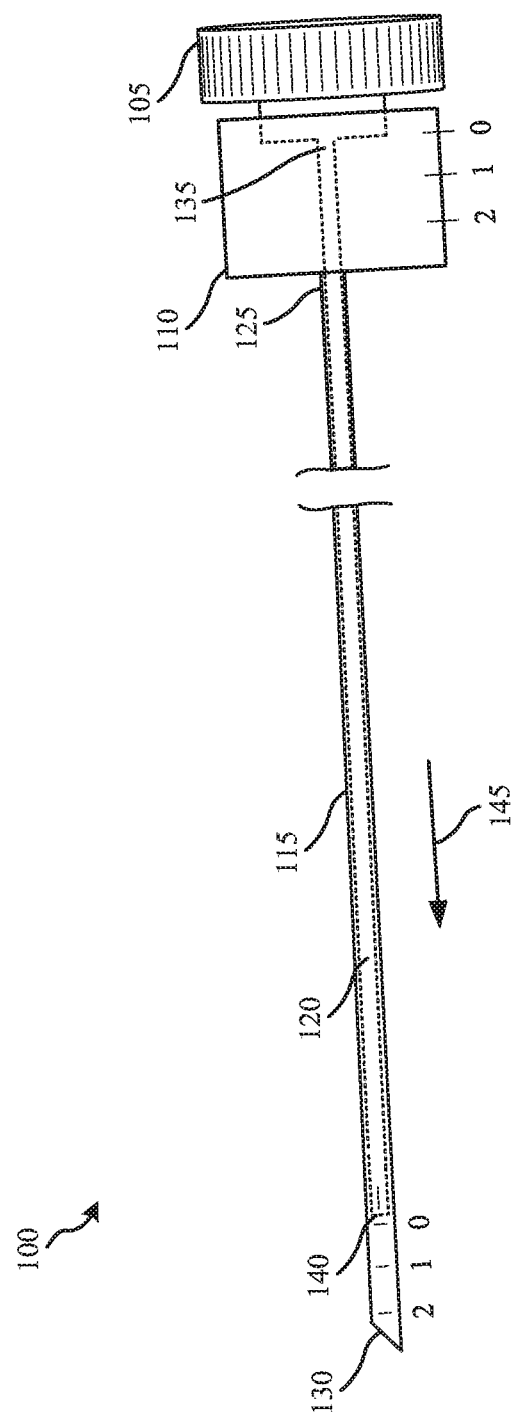
FIG. 1 is a schematic view of a fiducial marker delivery device in accordance with aspects of the present disclosure.

FIG. 1 illustrates a side view of a fiducial marker delivery device 100 in accordance with various examples of the present disclosure. The fiducial marker delivery device 100 includes a needle 115, a stylet 120, a stylet hub 105, and a stylet spacer 110. In some examples, the needle 115 is a Fine Needle Aspiration (FNA) needle with a sharpened distal end 130 and an internal lumen extending from the proximal end 125 to the distal end 130. The needle 115 may be manufactured from a variety of metallic or polymeric materials including, but not limited to, stainless steel or alloys thereof, nitinol or alloys thereof, poly-ether-ether ketone, polyamide, polyethersulfone, polyurethane, ether block amide copolymers, polyacetal, polytetrafluoroethylene, or derivatives thereof. The outer diameter of the needle 115 may range from 0.020 inches (0.5 mm) to 0.050 inches (1.3 mm) and the diameter of the internal lumen may range from 0.012 inches (0.30 mm) to 0.045 inches (1.14 mm). The length of the needle 115 depends upon the particular application and may range from 19.7 inches (500 mm) to 98.4 inches (2500 mm). In some examples, the outer surface of the distal portion of the needle 115 is roughened or otherwise treated to enhance the echogenicity or acoustic reflection of the distal portion of the needle 115 under endoscopic ultrasound (EUS) or similar visualization techniques.

The stylet 120 is generally a solid, flexible, metallic or polymeric rod configured to advance through the lumen of the needle 115. According to some examples, the outer diameter of the stylet 120 is continuous from the proximal end 135 to the distal end 140. In other examples, the outer diameter of the stylet 120 is tapered such that the distal end 140 has a smaller outer diameter than the proximal end 135. The stylet hub 105 is coupled with the proximal end 135 of the stylet 120 and provides a clinician with the means to grip and maneuver the stylet 120 through the needle 115. For example, the clinician may advance the stylet 120 distally and proximally through the lumen of the needle 115 by pushing or pulling on the stylet hub 105, respectively.

The stylet spacer 110 generally facilitates the controlled advancement of the stylet 120 through the needle 115 in the distal direction illustrated by arrow 145. According to various examples, the stylet spacer 110 includes a plurality of stopping features configured to engage with the stylet 120 or the stylet hub 105 to stop the distal end 140 of the stylet 120 at one or more predetermined distances from the distal end 130 of the needle 115. The stylet spacer 110 may also be adjustable between a plurality of positions that correspond to the plurality of predetermined distances from the distal end 130 of the needle 115.

For instance, with reference to FIG. 1, the stylet spacer 110 may be adjustable between three positions, referred to as positions 0, 1, and 2. When the stylet spacer 110 is in position 0, the stylet hub 105 is engaged with a first stopping feature of the stylet spacer 110 such that the distal end 140 of the stylet 120 is stopped at a first predetermined distance from the distal end 130 of the needle 115, referred to as location 0. The stylet spacer 110 may then be adjusted to position 1. According to various examples, the stylet spacer 110 is configured to provide tactile feedback to the clinician so that the clinician can feel the adjustment of the stylet spacer 110 between positions 0 and 1. In position 1, the stylet spacer 110 permits the stylet 120 to advance distally until the stylet hub 105 engages a second stopping feature of the stylet spacer 110, stopping the distal end 140 of the stylet 120 at location 1 within the needle 115. The stylet spacer 110 may also provide tactile feedback to the clinical once the stylet hub 105 engages with the second stopping feature so that the clinician knows when the distal end 140 of the stylet 120 reaches location 1.

The stylet spacer 110 may be further adjusted to position 2, which permits the stylet 120 to advance distally until the distal end 140 of the stylet 120 reaches location 2. Accordingly, the stylet spacer 110 allows the clinician to controllably advance the stylet 120 distally through the needle 115 while providing tactile feedback to the clinician once the stylet 120 reaches certain predetermined locations within the needle 115. Although a stylet spacer 110 configured for three positions is described, it may be appreciated that the stylet spacer 110 may be configured for any number of positions corresponding to any number of predetermined locations from the distal end 130 of the needle 115.

Figure 2:
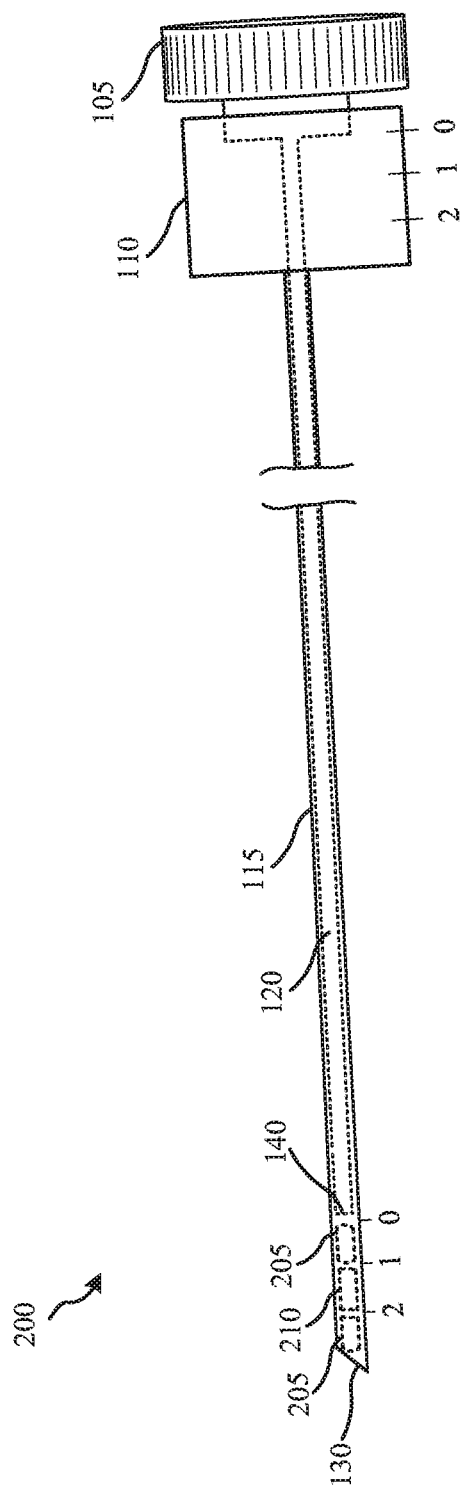
FIG. 2 is a schematic view of a fiducial marker delivery device in accordance with aspects of the present disclosure.

Referring to FIG. 2, a side view of a fiducial marker delivery device 200 is illustrated in accordance with various examples of the present disclosure. The fiducial marker delivery device 200 includes a needle 115, a stylet 120, a stylet hub 105, and a stylet spacer 110, and may be an example of the fiducial marker delivery device 100 described with reference to FIG. 1. The fiducial marker delivery device 200 also includes one or more preloaded fiducial markers 205 housed within the needle 115 near the distal end 130. In general, the fiducial markers 205 are made from biocompatible materials that are visible under endoscopic ultrasound (EUS) and image-guided radio therapy (IGRT) and are magnetic resonance (MR) conditional. In some examples, the fiducial markers 205 are gold cylinders, but other shapes and other biocompatible and radio-opaque materials may be used.

A device 200 with multiple preloaded fiducial markers 205 may advantageously reduce or eliminate the need to manually load the needle 115 with the fiducial markers 205 during the procedure, thereby reducing the duration of the procedure as well as the risks to the clinician associated with manually loading a contaminated needle 115 with a fiducial marker 205 (e.g., accidental needle stick).

In accordance with various aspects of the present disclosure, the fiducial marker delivery device 200 also includes one or more fiducial marker spacers 210 disposed between each of the preloaded fiducial markers 205. In general, the fiducial marker spacers 210 are implantable-grade materials such as bioabsorbable resin, polypropylene, polylactic acid (PLA), poly lactic-co-glycolic acid (PGLA), polyamide, poly-vinyl alcohol (PVOH) or any other similar biocompatible or bioabsorbable material or material blend. The fiducial marker spacers 210 are generally cylindrical in shape and may range in length from 0.079 inches (2 mm) to 0.393 inches (10 mm). Although two fiducial markers 205 are shown separated by a single fiducial marker spacer 210, it may be appreciated that additional fiducial markers 205 and fiducial marker spacers 210 may be used. For instance, six fiducial markers 205 may be preloaded into the needle 115 separated by five fiducial marker spacers 210.

As described with reference to FIG. 1, the stylet spacer 110 is configured to control the distal advancement of the stylet 120 through the needle 115 by stopping the distal end 140 of the stylet 120 at various locations distanced from the distal end 130 of the needle 115. When preloaded with a plurality of fiducial markers 205, a clinician is able to selectively deploy the fiducial makers 205 from the distal end 130 of the needle 115 by controllably advancing the stylet 120 with the stylet spacer 110. To controllably deploy the fiducial markers 205 with the stylet spacer 110, the predetermined locations within the needle 115 are based on the number and size of the fiducial markers 205 and fiducial marker spacers 210 housed within the needle 115. In general, the distances from the distal end 130 of the needle 115 of the various locations are selected such that a single fiducial marker 205 is deployed each time the stylet 120 is advanced to a new location. For example, with reference to FIG. 2, when the stylet spacer 110 is in position 0, the distal end 140 of the stylet 120 is stopped at location 0, which is distanced from the distal end 130 of the needle 115 such that there is sufficient room for all of the preloaded fiducial markers 205 and fiducial marker spacers 210. Accordingly, when in position 0, the stylet spacer 110 prevents any of the fiducial markers 205 or fiducial marker spacers 210 from being deployed. Position 0, then, may be referred to as the "safety" position and is used to prevent inadvertent deployment of the fiducial markers 205 during shipping and handling of the fiducial marker delivery device 200.

When the stylet spacer 110 is adjusted to position 1, the distal end 140 of the stylet 120 may advance distally until reaching location 1. The distance of location 1 from the distal end 130 of the needle 115 may be selected such that only the distal-most fiducial marker 205 is deployed from the needle 115. Position 1 may be referred to as a first deployed position. Alternatively, the distance of location 1 may be selected such that both the distal-most fiducial marker 205 and the distal-most fiducial marker spacer 210 is deployed. In either case, the stylet spacer 110 is configured to deploy only a single fiducial marker 205 in each deployed position. When the stylet spacer 110 is adjusted to position 2, the distal end 140 of the stylet 120 may advance distally until reaching the location 2. The distance of location 2 from the distal end 130 of the needle 115 may be selected such that only the second fiducial marker 205 is deployed or such that both the fiducial marker spacer 210 and the second fiducial marker 205 are deployed (if the distal-most fiducial marker spacer 210 was not already deployed). It may be appreciated that the stylet spacer 110 may be adapted for any number and size of fiducial markers 205 and fiducial marker spacers 210 as the particular application may require.

Figure 3:
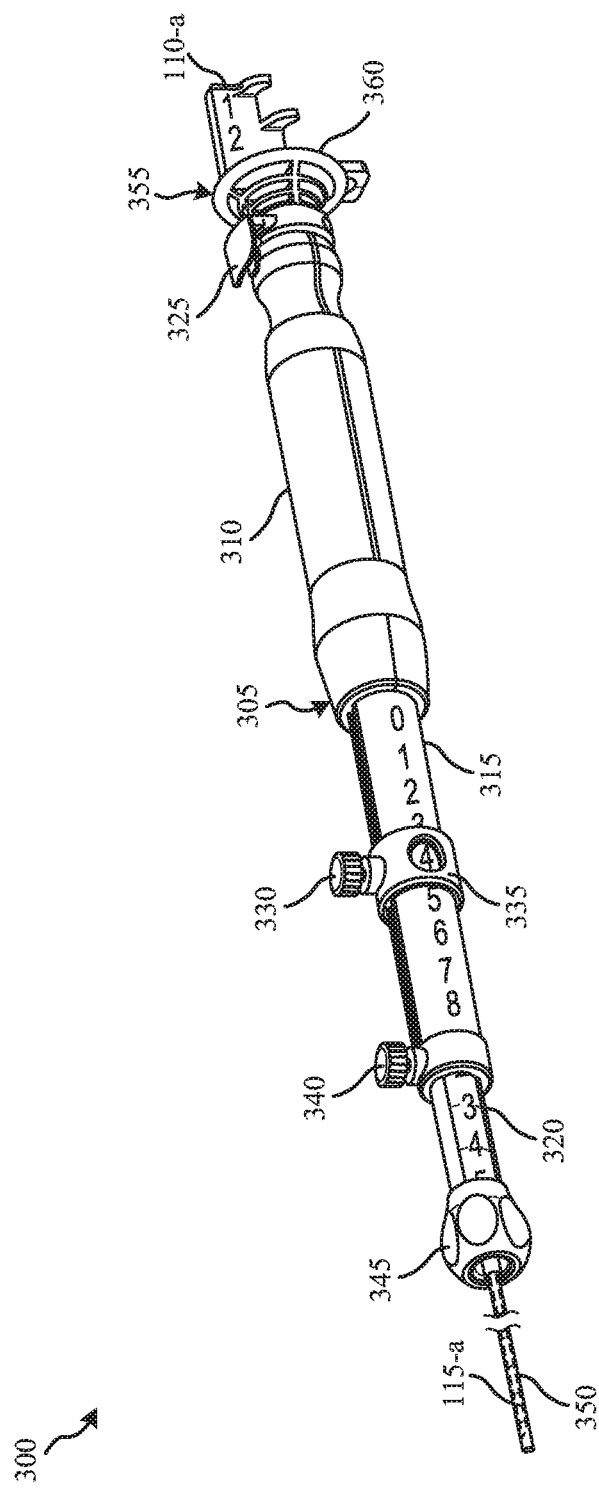
FIG. 3 is an illustration of a fiducial marker delivery device in accordance with aspects of the present disclosure.

FIG. 3 illustrates a perspective view of a fiducial marker delivery device 300 in accordance with various examples of the present disclosure. The fiducial marker delivery device 300 includes a handle assembly 305 and a needle assembly 355 (shown in detail in FIG. 4A). The handle assembly 305 includes a proximal handle member 310, a middle handle member 315, and a distal handle member 320. The proximal, middle, and distal handle members 310, 315, 320 each include an inner lumen and are coupled together to form a continuous lumen extending throughout the length of the handle assembly 305. The proximal handle member 310 is slidably disposed over at least a portion of the middle handle member 315, and, similarly, the middle handle member 315 is slidably disposed over at least a portion of distal handle member 320. The distal handle member 320 may also include a threaded connector element 345 configured to securely attach to a working channel of an endoscope (not shown). The fiducial marker delivery device 300 also includes a sheath 350 extending from the distal end of the distal handle member 320 and configured to extend through the working channel of an attached endoscope. The sheath 350 is generally made from a flexible polymeric material and provides a continuous conduit through which a needle or other elements may travel between the handle assembly 305 and the target tissue within the body. Accordingly, the length and diameter of the sheath 350 depend upon the particular application.

The needle assembly 355 (shown in detail in FIG. 4A) includes a needle 115-*a* and a needle hub 360 coupled with the proximal end of the needle 115-*a*. The needle 115-*a* extends from the needle hub 360, through the handle assembly 305, and into the sheath 350. The needle hub 360 is configured to releasably couple with the handle assembly 305. For example, a portion of the needle hub 360 may be inserted into the proximal end of the proximal handle member 310. A spring-loaded thumb latch 325 may retain the needle hub 306 in place. To release the needle hub 360 from the handle assembly 305, the clinician may depress the thumb latch 325 and pull the needle hub 360 proximally. Accordingly, the needle assembly 355 may be inserted into and removed from the handle assembly 305.

The handle assembly 305 may include one or more adjustment features that limit the sliding movement of the handle members 310, 315, 320 relative to each other. For instance, the handle assembly 305 may include a locking ring 335 with a threaded thumbscrew 330 disposed around the middle handle member 315. The locking ring 335 may be slid along the middle handle member 315 and tightened in a desired position with the thumbscrew 330. When tightened, the locking ring 335 limits the movement of the proximal handle member 310 in the distal direction relative to the middle handle member 315, thereby allowing the clinician to establish a set penetration depth of the needle 115-*a* beyond the distal end of the sheath 350. Similarly, a thumbscrew 340 is configured to lock the position of the distal handle member 320 with respect to the middle handle member 320, thereby allowing the clinician to establish a set extension depth of the sheath 350 beyond the distal end of an attached endoscope.

The fiducial marker delivery device 300 also includes a stylet spacer 110-*a* (shown in detail in FIG. 5), which may be an example of the stylet spacer 110 described with reference to FIGS. 1-2. As shown, the stylet spacer 110-*a* may be coupled with the needle hub 360. Alternatively, the stylet spacer 110-*a* may be coupled directly with the handle assembly 305. Particular features and functions of the stylet spacer 110-*a* are described in detail with reference to FIGS. 5-8.

Referring to FIG. 4A, a side view of the needle assembly 355 and the stylet spacer 110-*a* is illustrated in accordance with various examples of the present disclosure. In some examples, the stylet spacer 110-*a* is coupled with the needle assembly 355 and may be coupled directly to the needle hub 360. For example, the stylet spacer 110-*a* may be coupled with a mounting post 405 extending from the proximal end of the needle hub 360. As described in greater detail below, the connection between the stylet spacer 110-*a* and the mounting post 405 may facilitate the stylet spacer 110-*a* to rotate around the mounting post 405 and to slide, actuate, or otherwise move with respect to the mounting post 405 in a plane orthogonal to the mounting post 405. Also shown in FIG. 4A is a stylet 120-*a* and a stylet hub 105-*a* coupled with the proximal end of the stylet 120-*a*. The stylet 120-*a* extends from the stylet hub 105-*a*, through the mounting post 405, needle hub 360, and needle 115-*a*. FIG. 4B illustrates a detailed view of the stylet 120-*a* protruding from the distal end of the needle 115-*a*. As described in detail below, a clinician may control the distal advancement of the stylet 120-*a* through the needle 115-*a* by selectively engaging the stylet hub 105-*a* with one or more stopping features of the stylet spacer 110-*a*.

Figure 5:
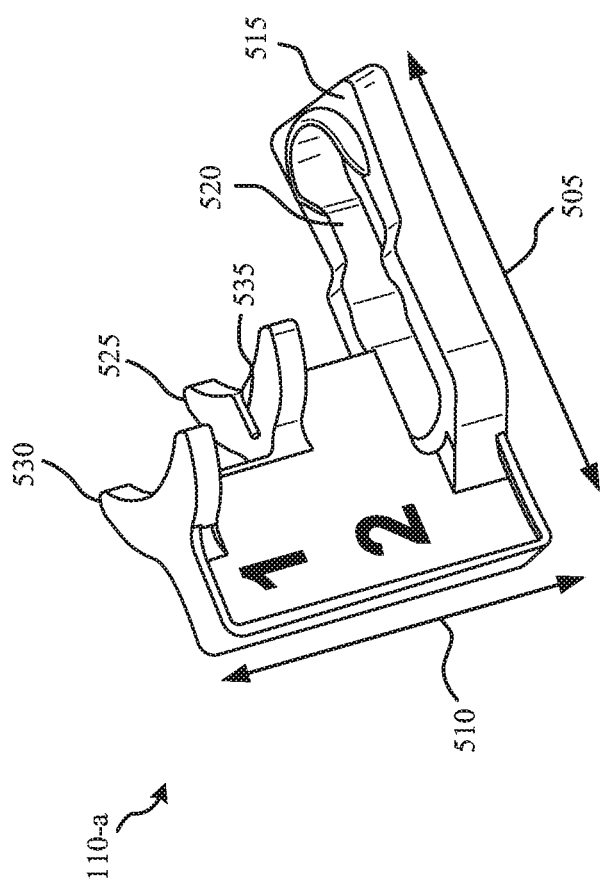
FIG. 5 is an illustration of a component of a fiducial marker delivery device in accordance with aspects of the present disclosure.

With reference to FIG. 5, a perspective view of the stylet spacer 110-*a* is illustrated in accordance with various examples of the present disclosure. The stylet spacer 110-*a* includes a base portion 505 and an upright portion 510 extending orthogonal to the base portion 505. The base portion 505 may include a channel 520 of removed material that extends through the entire thickness of the base portion 505. In general, the channel 520 serves as a coupling or mounting point between the stylet spacer 110-*a* and the needle assembly 355. For instance, the internal walls of the channel 520 may include one or more grooved portions that generally conform to the outer diameter of the mounting post 405 shown in FIG. 4A. Accordingly, the stylet spacer 110-*a* snaps into place when the mounting post 405 is within one of these grooved portions. The snapping interface between the grooved portions of the channel 520 and the mounting post 405 provides tactile feedback to the clinician indicating as the stylet spacer 110-*a* is adjusted between positions.

In accordance with various examples, the stylet spacer 110-*a* includes a plurality of stopping features configured to selectively engage with the stylet 120 or stylet hub 105. For example, the stopping features may include one or more flat surfaces upon which the stylet hub 105 may abut to. Referring to FIG. 5, the flat surfaces may include the top surface 515 of the base portion 505 and one or more ledges 525, 530 spaced at various distances from the base portion 505. Although two ledges 525, 530 are illustrated, it may be appreciated that the stylet spacer 110-*a* may include additional ledges as required by the particular application. The ledges 525, 530 may be arranged in a stair-step configuration as shown and may include various other features to interface with the components of a stylet 120 or a stylet hub 105. For example, as shown, the ledges 525, 530 may include a concave portion sized to conform to the outer diameter of a portion of a stylet hub 105. Also, one or more of the ledges 525, 530 may include a slot 535 sized to allow the stylet 120 to slide through.

Figure 6A:
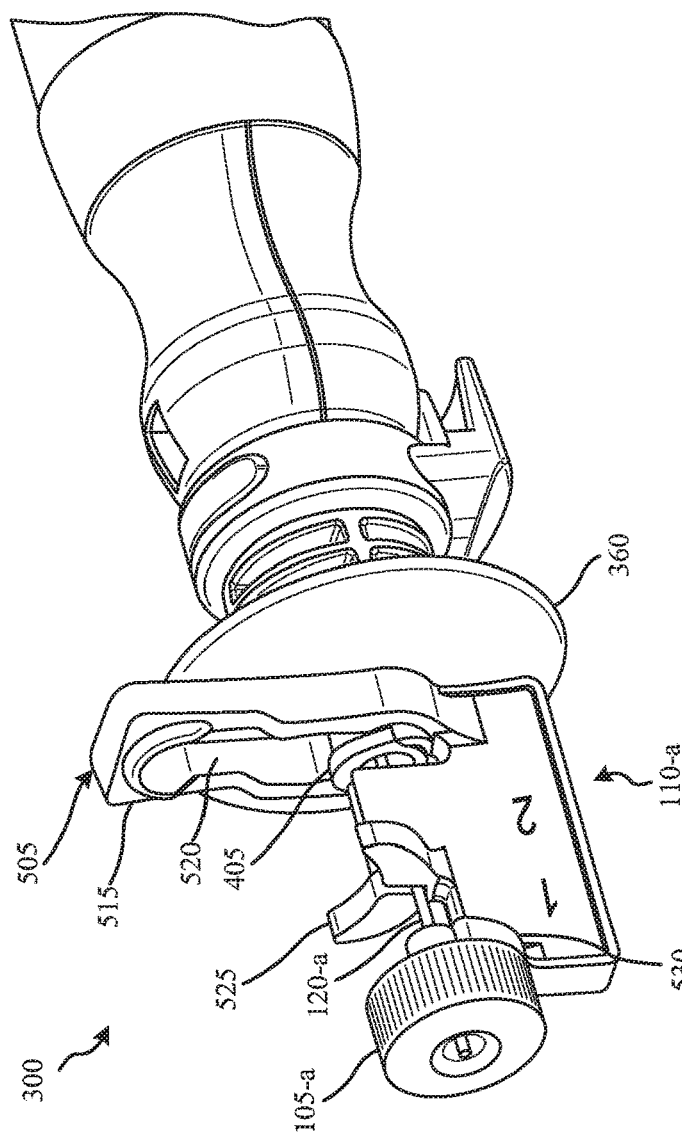
FIG. 6A is an illustration of a proximal portion of a fiducial marker delivery device in accordance with aspects of the present disclosure.

FIG. 6A illustrates a perspective view of the proximal portion of the fiducial marker delivery system 300 described with reference to FIG. 3. In general, the stylet spacer 110-*a* facilitates the controlled advancement of the stylet 120-*a* distally through the needle 115-*a*. According to various examples, the stylet spacer 110-*a* is adjustable between several positions and includes one or more stopping features configured to engage with the stylet 120-*a* or stylet hub 105-*a* in each of the several positions. Moreover, each of the positions of the stylet spacer 110-*a* may correspond with a resting location of the distal end 140 of the stylet 120-*a* within the needle 115-*a*. For example, with reference to FIG. 6A, the stylet spacer 110-*a* is illustrated in the safety position (referred to as position 0 in FIGS. 1-2). In the safety position, the stylet hub 105-*a* may abut with or otherwise engage with the ledge 530 of stylet spacer 110-*a*. The ledge 530 prevents the stylet hub 105-*a* and the stylet 120-*a* from advancing distally through the needle 115-*a*.

Figure 6B:
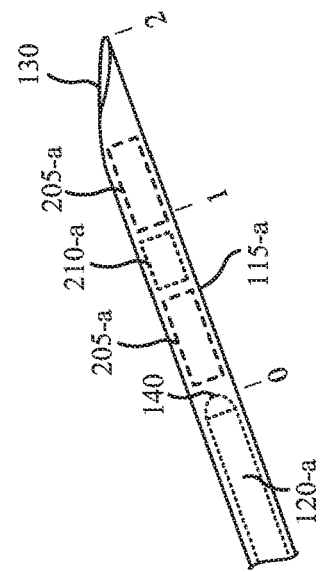
FIG. 6B is an illustration of a distal portion of a fiducial marker delivery device in accordance with aspects of the present disclosure.

Referring to FIG. 6B, when the stylet spacer 110-*a* is in the safety position, the distal end 140 of the stylet 120-*a* is stopped at a first predetermined distance from the distal end 130 of the needle 115-*a* referred to as location 0. Thus, when the stylet spacer 110-*a* is in the safety position, none of the preloaded fiducial markers 205-*a* or fiducial marker spacers 210-*a* are deployed.

Figure 7B:
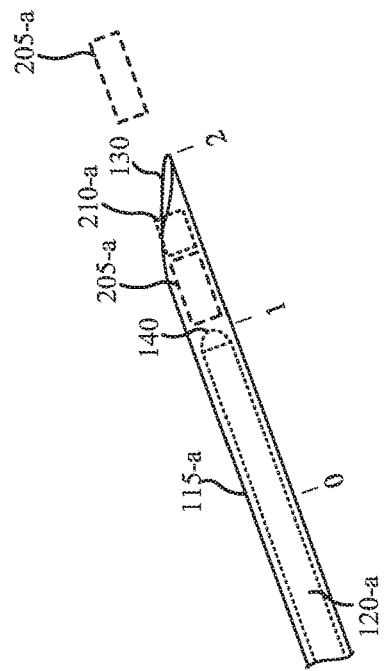
FIG. 7B is an illustration of a distal portion of a fiducial marker delivery device in accordance with aspects of the present disclosure.
Figure 7A:
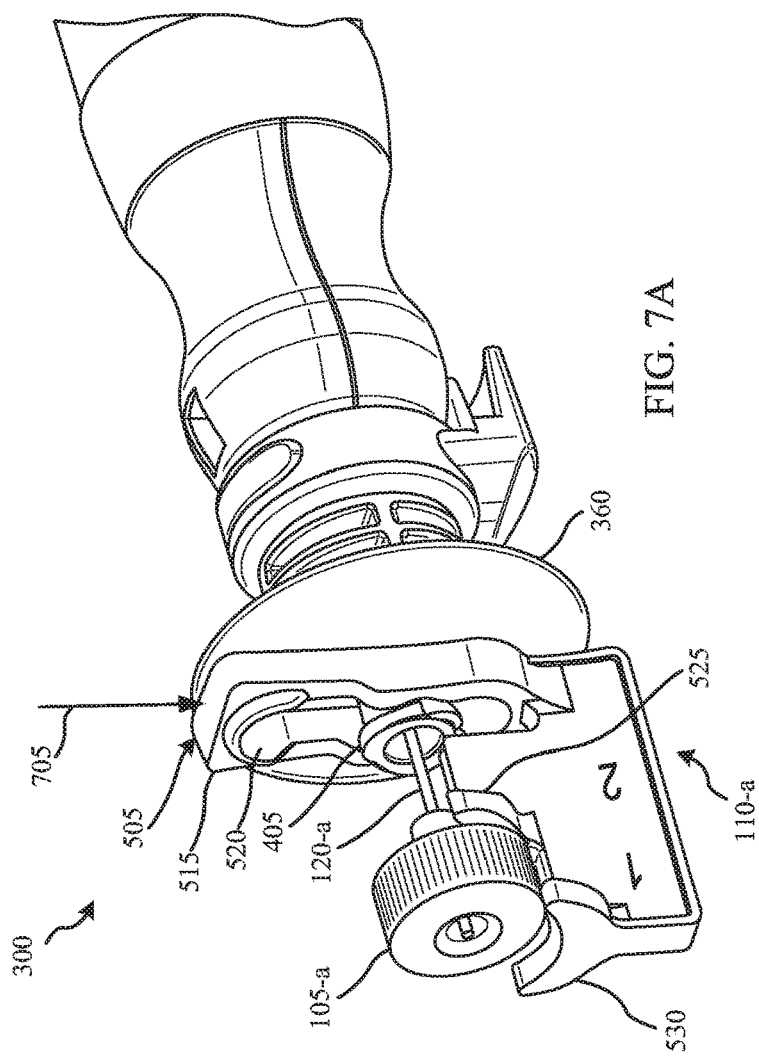
FIG. 7A is an illustration of a proximal portion of a fiducial marker delivery device in accordance with aspects of the present disclosure.

With reference to FIG. 7A, the stylet spacer 110-*a* is illustrated in a first deployed position (referred to as position 1 in FIGS. 1-2). A clinician may adjust the stylet spacer 110-*a* between the safety position illustrated in FIG. 6A, and the first deployed position illustrated in FIG. 7A by pushing the stylet spacer 110-*a* in a direction illustrated by arrow 705. Because of the fit between the grooved portions within the channel 520 and the mounting post 405, the clinician will be able to feel the stylet spacer 110-*a* dislodge from the safety position and snap into the first deployed position. This tactile feedback from the stylet spacer 110-*a* eliminates the need to visualize the stylet spacer 110-*a* during fiducial marker deployment, thereby allowing the clinician to continually monitor the distal end of the deployment device under EUS. As shown, the stylet spacer 110-*a* slides relative to mounting post 405 in a plane orthogonal to the mounting post 405. Once the stylet spacer 110-*a* has been adjusted from the safety position to the first deployed position, the stylet hub 105-*a* is free to advance distally towards the needle hub 306 until reaching a stopping feature such as ledge 525. The ledge 525 prevents the stylet hub 105-*a* and the stylet 120-*a* from advancing distally while the stylet spacer 110-*a* is in first deployed position.

FIG. 7B illustrates the placement of the stylet 120-*a* within the needle 115-*a* when the stylet spacer 110-*a* is in the first deployed position. As shown, the distal end 140 of the stylet 120-*a* is permitted to advance distally until reaching the location 1, which results in the deployment of the distal-most fiducial marker 205-*a*. Alternatively, location 1 may be selected such that both the distal-most fiducial marker 205-*a* and the fiducial marker spacer 210 are deployed when the stylet spacer 110-*a* is in the first deployed position. It may be appreciated that the distance between the ledge 530 and the ledge 525 corresponds to the distance traveled by distal end 140 of the stylet 120-*a*. Accordingly, the distances between the stopping features of the stylet spacer 110-*a* may be adjusted or calibrated to yield the desired distal displacement of the stylet 120-*a*, which may be based on the number and size of fiducial markers 205-*a* and fiducial marker spacers 210-*a* housed within the needle 115-*a*.

Figures 8A, 8B:
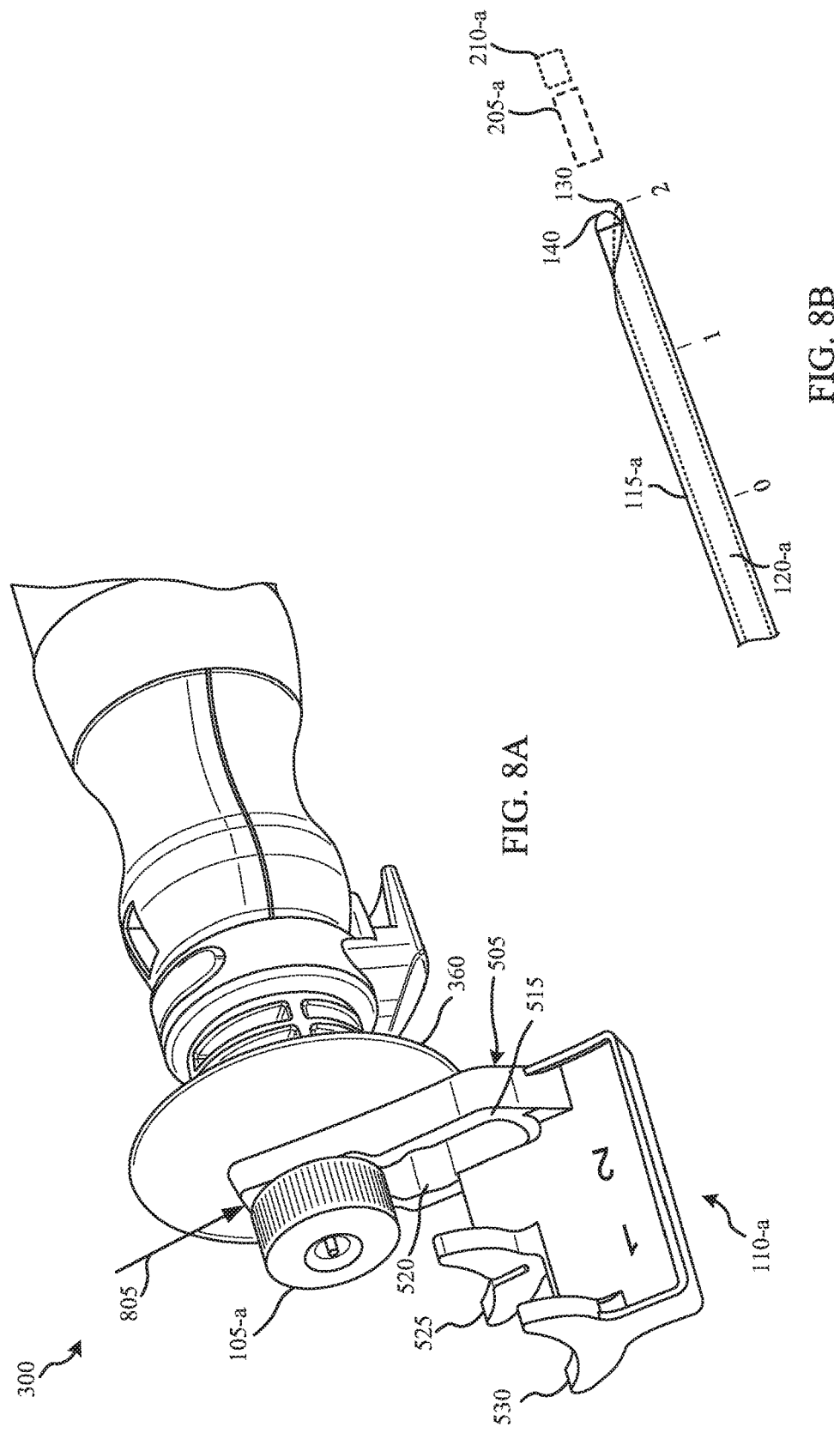
FIG. 8A is an illustration of a proximal portion of a fiducial marker delivery device in accordance with aspects of the present disclosure.
FIG. 8B is an illustration of a distal portion of a fiducial marker delivery device in accordance with aspects of the present disclosure.

Referring to FIG. 8A, the stylet spacer 110-*a* is illustrated in a second deployed position (referred to as position 2 in FIGS. 1-2). The clinician may adjust the stylet spacer 110-*a* from the first deployed position to the second deployed position by pushing the stylet spacer 110-*a* in a direction shown by arrow 805. The stylet spacer 110-*a* is configured to dislodge from the first deployed position and snap into the second deployed position similar to the transition from the safety to first deployed positions. In the second deployed position, the stylet hub 105-*a* is free to advance distally towards the needle hub 360 until reaching a stopping feature such as the top surface 515 of the base portion 505. Alternatively, the stopping feature may be the top portion of the mounting post 405. In such examples, both the mounting post 405 and the stylet hub 105-*a* may be threaded (e.g., a luer connection) so that the clinician can lock the stylet hub 105-*a* to the mounting post 405 while the stylet spacer 110-*a* is in the second deployed position to ensure complete deployment of the second fiducial marker 205-*a*. In any case, as the stylet 120-*a* advances distally, it deploys the fiducial marker spacer 210-*a* and a second fiducial marker 205-*a* from the distal end 130 of the needle 115-*a* as illustrated in FIG. 8B. Although the described example was configured to deploy two preloaded fiducial markers 205-*a*, it may be appreciated that the stylet spacer 110-*a* may be adapted to include additional stopping features and/or additional positions such that additional preloaded fiducial markers 205-*a* may be deployed.

Figure 9C:
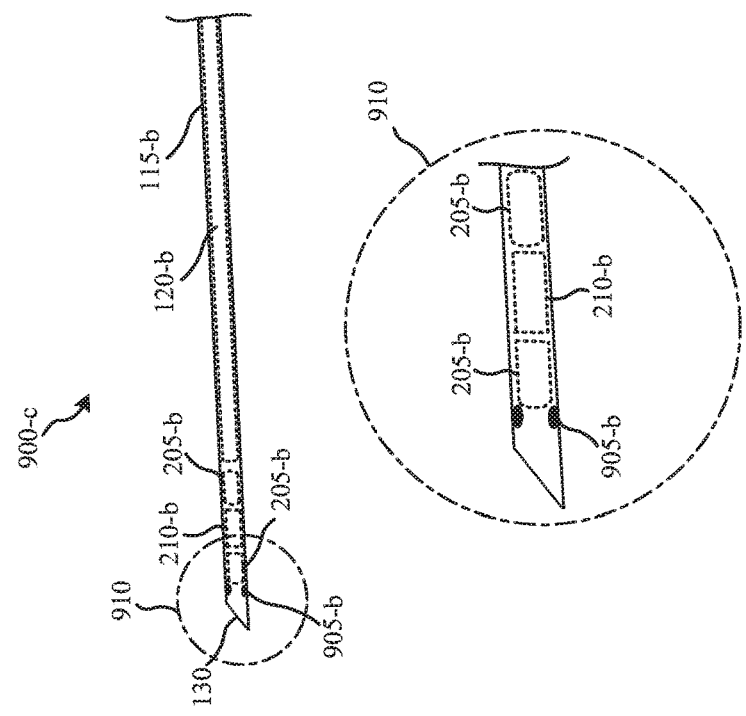
FIG. 9C is an illustration of a distal portion of a fiducial marker delivery device in accordance with aspects of the present disclosure.
Figure 9A:
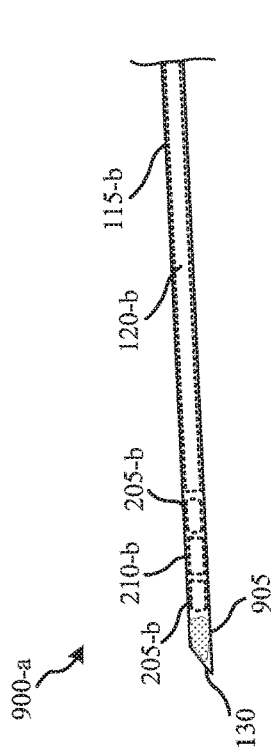
FIG. 9A is an illustration of a distal portion of a fiducial marker delivery device in accordance with aspects of the present disclosure.

With reference to FIG. 9A, the distal portion of a fiducial marker delivery device 900-*a* is illustrated in accordance with various examples of the present disclosure. The fiducial marker delivery device 900-*a* includes a needle 115-*b*, a stylet 120-*b*, a plurality of fiducial markers 205-*b*, one or more fiducial marker spacers 210-*b*, and a fiducial marker retention member 905. In general, the fiducial marker retention member 905 is configured to help prevent the fiducial markers 205-*b* and spacers 210-*b* from inadvertently deploying from the needle 115-*b* while the stylet spacer 110 is in the safety position. In some examples, the fiducial marker retention member 905 is bone wax inserted into the distal end 130 of the needle 115-*b*. The bone wax 905 is deployed into the target tissue during deployment of the distal-most fiducial marker 205-*b*.

Figure 9B:
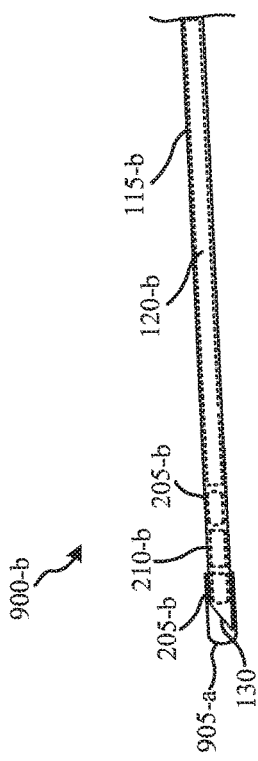
FIG. 9B is an illustration of a distal portion of a fiducial marker delivery device in accordance with aspects of the present disclosure.

FIG. 9B illustrates an alternative example of a fiducial marker retention member 905-*a*. Fiducial marker retention member 905-*a* may be a cap placed over the distal end 130 of the needle 115-*b* and configured to prevent the inadvertent deployed of the fiducial markers 205-*b*. In some examples, the cap 905-*a* is made from a bio-compatible, dissolvable material. For example, polyvinyl alcohol or other similar dissolvable polymers may be used. In such examples, when the needle 115-*b* is inserted into the target tissue, the heat and/or moisture of the tissue dissolves the cap 905-*a*, thereby allowing the deployment of the preloaded fiducial markers 205-*b*. Alternatively, the cap 905-*a* may be removed just prior to the needle 115-*b* being inserted into the target tissue.

FIG. 9C illustrates yet another alternative fiducial marker retention member 905-*b* in accordance with various aspects of the present disclosure. The fiducial marker retention member 905-*b* includes one or more detent features extending inward from the lumen wall of the needle 115-*b* (as illustrated in detailed view 910). In general, the detent features 905-*b* are configured to prevent the fiducial markers 205-*b* and/or the fiducial marker spacers 210-*b* from inadvertently falling out of the distal end 130 of the needle 115-*b* by partially blocking the lumen of the needle 115-*b*. The detent features 905-*b* may be formed by swaging the outside surface of the needle 115-*b*, thereby creating small detent constrictions on the internal diameter of the lumen of the needle 115-*b*. In other examples, additional material may be adhered or otherwise formed onto the internal diameter of the lumen of the needle 115-*b* to form the one or more detent features 905-*b*. The detent features 905-*b* may be permanently formed inside the needle 115-*b*. In any case, the detent features 905-*b* are configured to provide an amount of frictional resistance between the detent features 905-*b* and the fiducial markers 205-*b* and/or the fiducial marker spacers 210-*b* that can be overcome by a clinician while advancing the stylet distally, but that prevents the accidental fall out of the fiducial markers 205-*b* and/or the fiducial marker spacers 210-*b*.

In some examples, there may be one or more sets of two or more detent features 905-*b* extending inwardly from equally-spaced radial locations within the needle 115-*b*. Although one set of detent features 905-*b* is shown, it is envisioned that multiple sets of two or more detent features 905-*b* may be added. For example, a set of two or more detent features 905-*b* may be placed distal to each preloaded fiducial marker 205-*b* and/or each fiducial marker spacer 210-*b*. Alternatively, instead of sets of two or more detents 905-*b*, there may be one or more discrete detent features 905-*b* extending inwardly from the lumen of the needle 115-*b*. For example, there may be a single-point detent feature 905-*b* located near the distal end 130 of the needle 115-*b* or there may be a single-point detent feature 905-*b* located distal to each fiducial marker 205-*b* and/or each fiducial marker spacer 210-*b*. In yet another example, a single detent feature 905-*b* may form an internal ridge completely circumscribing the internal diameter of the lumen of the needle 115-*b*. In addition, combinations of these various types of detent features 905-*b* may be used.

Figure 10A:
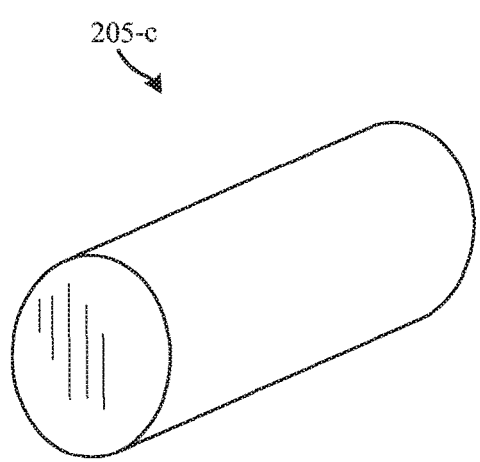
FIG. 10A is an illustration of a fiducial marker in accordance with aspects of the present disclosure.
Figure 10B:
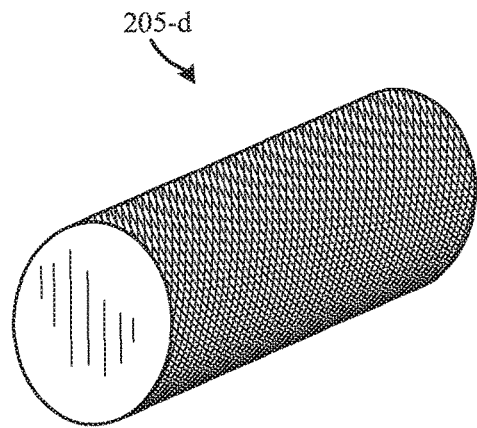
FIG. 10B is an illustration of a fiducial marker in accordance with aspects of the present disclosure.
Figure 10C:
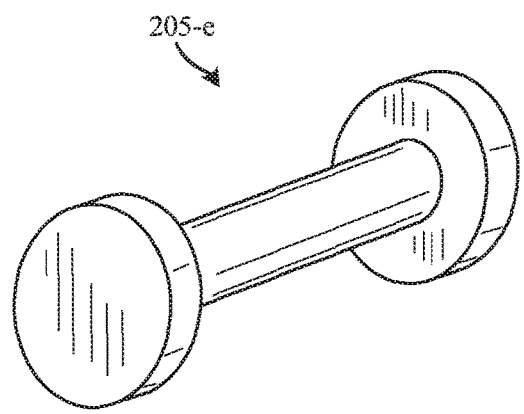
FIG. 10C is an illustration of a fiducial marker in accordance with aspects of the present disclosure.

FIGS. 10A-10C illustrate various examples of fiducial markers 205 according to certain aspects of the present disclosure. As shown in FIG. 10A, a fiducial marker 205-*c* may be cylindrical with a relatively smooth surface and may range in length from 0.12 inches (3 mm) to 0.79 inches (20 mm). In an alternative example illustrated in FIG. 10B, the outer surface of the fiducial marker 205-*d* may be roughened with a knurling, sandblasting, swaging, or other similar technique. The roughened surface may increase the acoustic reflectivity and thereby enhance the visibility of the fiducial marker 205-*d* under EUS. The roughened surface may also reduce migration of the fiducial marker 205-*d* within the target tissue due to the increased friction between the surface of the fiducial marker 205-*d* and the tissue.

Additionally or alternatively, the profile of the fiducial marker may be non-cylindrical. For example, as illustrated in FIG. 10C, the fiducial marker 205-*e* may be dogbone-shaped, which may reduce migration of the fiducial marker 205-*c* within the target tissue. The dogbone shape of the fiducial marker 205-*e* also reduces the amount of potential surface area overlap between the fiducial marker 205-*e* and the inner lumen of the needle 115, thereby reducing friction and the corresponding deployment force needed to deploy the fiducial marker 205-*e* from the needle 115.

Figure 11:
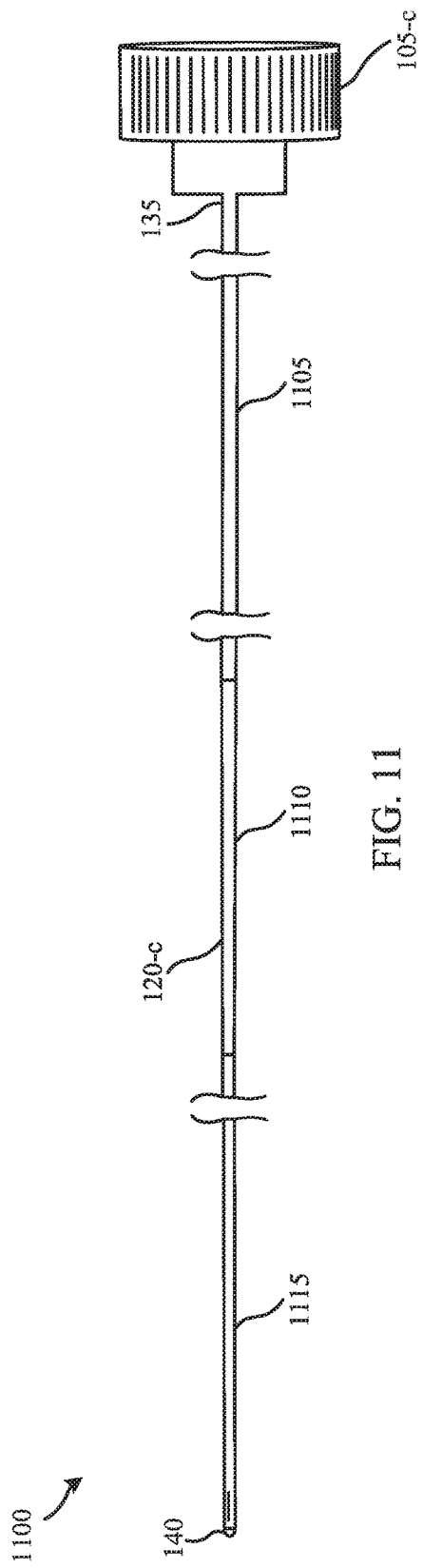
FIG. 11 is an illustration of a subassembly of a fiducial marker delivery device in accordance with aspects of the present disclosure.

With reference to FIG. 11, a side view of a stylet assembly 1100 is illustrated in accordance with various examples of the present disclosure. The stylet assembly 1100 may be used with any of the fiducial marker deployment devices described with reference to FIGS. 1-3. The stylet assembly 1100 includes a tapered stylet 120-*c* coupled at its proximal end with a stylet hub 105-*c*. The tapered stylet 120-*c* includes a proximal portion 1105 with a first diameter D1, a distal portion 1115 with a second diameter D2, and a tapered portion 1110 connecting the proximal and distal portions. According to various examples, the diameter D1 of the proximal portion 1105 is greater than the diameter D2 of the distal portion 1115. The tapered portion 1110 may be gradual as shown, or may be instead stepped between the D1 and D2. In general, the larger diameter D1 of the proximal portion is configured to provide the necessary columnar strength to push the one or more preloaded fiducial markers 205 and fiducial marker spacers 210 from the needle 115, whereas the smaller diameter D2 is configured to reduce the frictional force between the distal portion 1115 of the stylet 120-c and the inside of the needle 115, especially when the distal portion of the needle is tightly bent.

Figure 12:
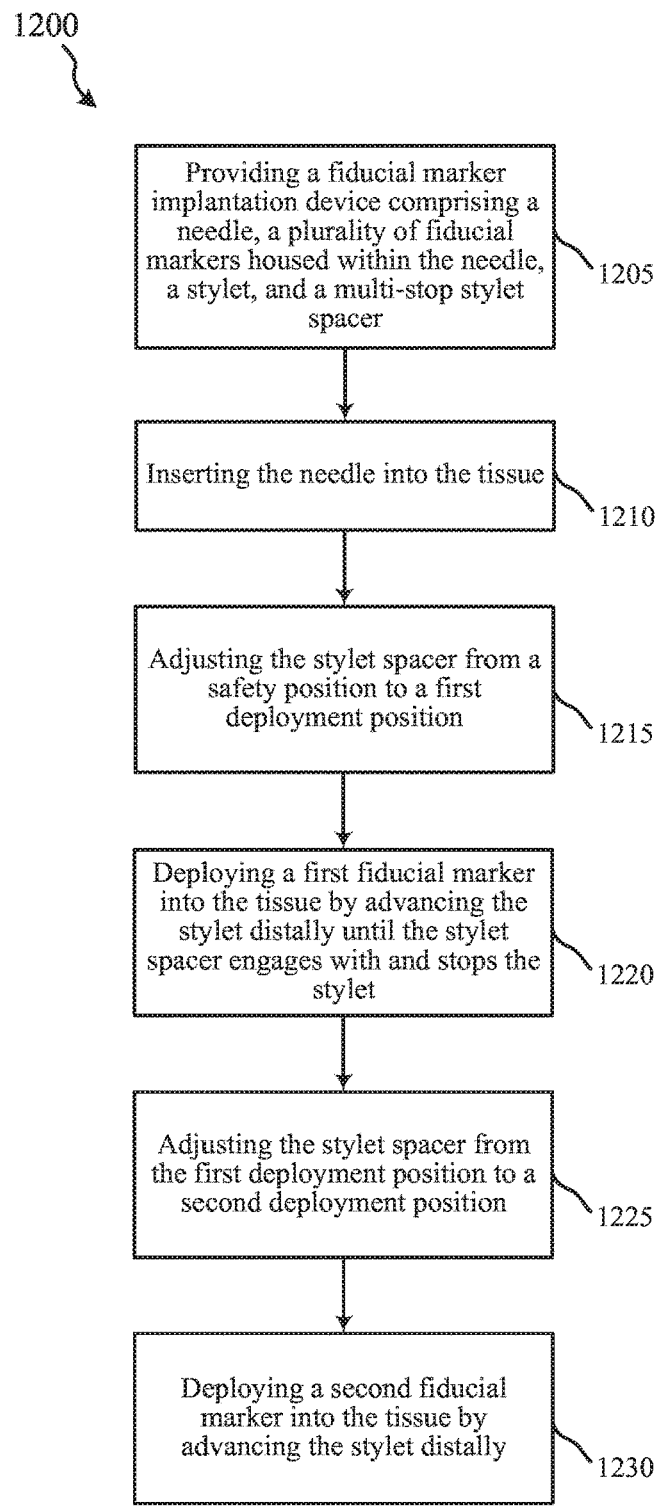
FIG. 12 is a flow chart illustrating a method in accordance with aspects of the present disclosure.

FIG. 12 is a flow chart illustrating an example of a method 1200 for delivering or implanting a plurality of fiducial markers into a tissue in accordance with various examples of the present disclosure.

At block 1205, the method 1200 may include providing a fiducial marker implantation device, such as any of devices 100, 200, or 300, with a needle 115, a plurality of fiducial markers 205 housed within the needle 115, a stylet 120, and a stylet spacer 110.

At block 1210, the method 1200 may include inserting the needle 115 into the tissue. According to certain aspects, the needle 115 may be percutaneously inserted into the tissue. In other examples, the needle 115 is inserted through a natural opening in the body, such as into the patient's mouth, through a fiducial marker delivery device that interfaces with an endoscope. For example, the fiducial marker delivery device 300 described with reference to FIG. 3 may be used.

At block 1215, the method 1200 may include adjusting the stylet spacer 110 from a safety position to a first deployment position. According to various examples, the stylet spacer 110 is adjusted from the safety position by pushing on the stylet spacer, as described with reference to FIG. 7A.

At block 1220, the method 1200 may include deploying a first fiducial marker 205 into the tissue by advancing the stylet 120 distally until the stylet spacer 110 engages with and stops the stylet 120.

At block 1225, the method 1200 may include adjusting the stylet spacer 110 from the first deployment position to a second deployment position. According to various examples, the stylet spacer 110 is adjusted from the first deployment position to the second deployment position by pushing on the stylet spacer, as described with reference to FIG. 8A.

At block 1230, the method 1200 may include deploying a second fiducial marker 205 into the tissue by advancing the stylet 120 distally. In some examples, the stylet 120 is advanced distally until the stylet hub 105 engages with either a mounting post 405 or a third stopping feature of the stylet spacer 110, as described with reference to FIG. 8A. In accordance with various examples, the stylet spacer 110 may include a plurality of stopping features that engage with and stop the stylet 120 in each of the safety and first deployment positions.

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

The invention claimed is:

1. A device for implanting a plurality of fiducial markers into a tissue, comprising:
    a needle having a proximal end, a distal end, and a lumen extending therebetween;
    a stylet having a proximal end, a distal end, and a proximal hub attached to the proximal end, wherein the distal end is sized to slide within the lumen of the needle; and
    a multi-stop stylet spacer having a plurality of stopping features arranged in a stair-stepped configuration and configured to engage with the proximal hub of the stylet and stop the distal end of the stylet at a plurality of predetermined distances from the distal end of the needle, wherein:
        the multi-stop stylet spacer is adjustable between a plurality of positions by translating, relative to the stylet, the multi-stop stylet spacer in a plane orthogonal to a longitudinal axis of the stylet;
        in a first position, a first stopping feature engages with the proximal hub and prevents distal movement of the stylet;
        in a second position, the first stopping feature disengages from the proximal hub and allows distal movement of the stylet until a second stopping feature engages with the proximal hub and prevents distal movement of the stylet, wherein the multi-stop stylet spacer translates from the first position to the second position along the plane orthogonal to the longitudinal axis of the stylet; and
        in a third position, the second stopping feature disengages from the proximal hub and allows distal movement of the stylet until a third stopping feature engages with the proximal hub and prevents distal movement of the stylet, wherein the multi-stop stylet spacer translates from the second position to the third position along the plane orthogonal to the longitudinal axis of the stylet.

2. The device of claim 1, further comprising a plurality of fiducial markers housed within the lumen of the needle, wherein:
    in the first position the first stopping feature prevents deployment of any of the plurality of fiducial markers from the distal end of the needle; and
    in the second position the second stopping feature permits the deployment of a first of the plurality fiducial markers while preventing the deployment of a second of the plurality of fiducial markers.

3. The device of claim 1, wherein the plurality of predetermined distances are based on a number and a size of a plurality of fiducial markers housed within the lumen of the needle.

4. The device of claim 1, further comprising a plurality of fiducial markers housed within the lumen of the needle separated by at least one fiducial marker spacer.

5. The device of claim 1, further comprising a fiducial marker retention member coupled with the distal end of the needle.

6. The device of claim 5, wherein the fiducial marker retention member comprises bone wax.

7. The device of claim 5, wherein the fiducial marker retention member comprises a cap configured to fit over the distal end of the needle.

8. The device of claim 5, wherein the fiducial marker retention member comprises one or more detents disposed within the lumen of the needle.

9. The device of claim 1, wherein the stylet is tapered such that the distal end has a smaller diameter than the proximal end.

10. A system for implanting a plurality of fiducial markers into a tissue, comprising:
 a handle member assembly having a proximal end, a distal end, and a lumen extending therebetween;
 a sheath having a proximal end, a distal end, and a lumen extending therebetween, the proximal end of the sheath being coupled with the distal end of the handle member assembly forming a continuous lumen from the proximal end of the handle member to the distal end of the sheath;
 a needle having a proximal end, a distal end, and a lumen extending therebetween and being sized to advance through the continuous lumen of the handle member assembly and the sheath;
 a plurality of fiducial markers housed within the lumen of the needle;
 a stylet having a proximal end, a distal end, and a proximal hub attached to the proximal end and sized to advance through the lumen of the needle; and
 a multi-stop stylet spacer having a plurality of stopping features arranged in a stair-stepped configuration configured to engage with the proximal hub of the stylet and controllably deploy the plurality of fiducial markers from the distal end of the needle, wherein:
  the multi-stop stylet spacer is adjustable between a plurality of positions by translating, relative to the stylet, the multi-stop stylet spacer in a plane orthogonal to a longitudinal axis of the stylet;
  in a first position, a first stopping feature engages with the proximal hub and prevents distal movement of the stylet;
  in a second position, the first stopping feature disengages from the proximal hub and allows distal movement of the stylet until a second stopping feature engages with the proximal hub and prevents distal movement of the stylet, wherein the multi-stop stylet spacer translates from the first position to the second position along the plane orthogonal to the longitudinal axis of the stylet; and
  in a third position, the second stopping feature disengages from the proximal hub and allows distal movement of the stylet until a third stopping feature engages with the proximal hub and prevents distal movement of the stylet, wherein the multi-stop stylet spacer translates from the second position to the third position along the plane orthogonal to the longitudinal axis of the stylet.

11. The system of claim 10, wherein a first of the plurality of stopping features engages with the stylet to prevent the stylet from deploying any of the plurality of fiducial markers from the distal end of the needle.

12. The system of claim 11, wherein a second of the plurality of stopping features engages with the stylet to permit the stylet to deploy a first fiducial marker from the distal end of the needle, and wherein a third of the plurality of stopping features engages with the stylet to permit the stylet to deploy a second fiducial marker from the distal end of the needle.

13. The system of claim 10, wherein the multi-stop stylet spacer is adjustable between three positions, wherein:
 in the first position the proximal end of the stylet engages the first stopping feature to stop the distal end of the stylet to prevent any of the plurality of fiducial markers from being deployed from the distal end of the needle;
 in the second position the proximal end of the stylet engages the second stopping feature to stop the distal end of the stylet to permit the deployment of a first of the plurality fiducial markers while preventing the deployment of a second of the plurality of fiducial markers; and
 in the third position the proximal end of the stylet engages the third stopping feature to stop the distal end of the stylet to permit the deployment of the second of the plurality of fiducial markers.

14. The system of claim 10, further comprising at least one fiducial marker spacer disposed between at least two of the plurality of fiducial markers.

* * * * *